United States Patent
Chae et al.

(10) Patent No.: US 9,439,849 B2
(45) Date of Patent: Sep. 13, 2016

(54) COMPOSITION FOR PREVENTING OR ALLEVIATING SKIN WRINKLES CONTAINING HONEYBUSH EXTRACT OR FERMENTED HONEYBUSH AS AN ACTIVE INGREDIENT

(75) Inventors: Sungwook Chae, Daejeon (KR);
Hwa-Jung Choi, Daejeon (KR);
Jae-Hyoung Song, Chungcheongnam-do (KR); Goya Choi, Daejeon (KR); Mi Young Lee, Daejeon (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 0 days.

(21) Appl. No.: 14/233,567

(22) PCT Filed: Jul. 11, 2012

(86) PCT No.: PCT/KR2012/005503
§ 371 (c)(1),
(2), (4) Date: Jan. 17, 2014

(87) PCT Pub. No.: WO2013/012197
PCT Pub. Date: Jan. 24, 2013

(65) Prior Publication Data
US 2014/0127189 A1    May 8, 2014

(30) Foreign Application Priority Data
Jul. 18, 2011   (KR) .................. 10-2011-0070920

(51) Int. Cl.
| A61K 35/00 | (2006.01) |
| A61K 8/97 | (2006.01) |
| A61Q 19/08 | (2006.01) |
| A61K 8/42 | (2006.01) |
| A61K 8/60 | (2006.01) |
| A61K 8/64 | (2006.01) |
| A61K 8/65 | (2006.01) |
| A61K 8/67 | (2006.01) |
| A23L 1/30 | (2006.01) |
| A61K 8/99 | (2006.01) |
| A61K 35/744 | (2015.01) |
| A61K 36/48 | (2006.01) |

(52) U.S. Cl.
CPC .............. *A61K 8/97* (2013.01); *A23L 1/3002* (2013.01); *A61K 8/42* (2013.01); *A61K 8/606* (2013.01); *A61K 8/64* (2013.01); *A61K 8/65* (2013.01); *A61K 8/671* (2013.01); *A61K 8/99* (2013.01); *A61K 35/744* (2013.01); *A61K 36/48* (2013.01); *A61Q 19/08* (2013.01); *A61K 2236/19* (2013.01)

(58) Field of Classification Search
CPC ................................................... A61K 35/00
See application file for complete search history.

(56) References Cited

U.S. PATENT DOCUMENTS
2007/0264390 A1*  11/2007  Pretorius ................. 426/49

FOREIGN PATENT DOCUMENTS
| EP | 2 057 981 A1 | 5/2009 |
| FR | 2 879 446 A1 | 6/2006 |
| WO | 03/092413 A1 | 11/2003 |
| WO | 2010/000577 A2 | 1/2010 |
| WO | WO 2010/000577 | * 7/2010 ............. A61K 36/48 |

OTHER PUBLICATIONS

Feskanich et al. (Calcium, vitamin D, milk consumption, and hip fractures: a prospective study among postmenopausal women. The American Journal of Clinical Nutrition (2003); 77:504-11).*
Im et al., "Magnolol reduces UVB-induced photodamage by regulating matrix metalloproteinase activity", Environmental Toxicology and Pharmacology, vol. 39, pp. 417-423, (2015).
Im et al., "Anti-wrinkle effects of fermented and non-fermented Cyclopia intermedia in hairless mice", BMC Complementary and Alternative Medicine, vol. 14, p. 424 (pp. 1-6), (2014).
Kim et al., "Inhibition of UVB-induced wrinkle formation and MMP-9 expression by mangiferin isolated from Anemarrhena asphodeloides", European Journal of Pharmacology, vol. 689, pp. 38-44, (2012).
Song et al., "Protective effect of mango (*Mangifera indica* L.) against UVB-induced skin aging in hairless mice", Photodermatol Photoimmunol Photomed, vol. 29, pp. 84-89, (2013).
"Night Relax Anti-Age Power Serum", MINTEL, 10 pages, (Nov. 2010).
"Pure Transformation Night Treatment", MINTEL, 12 pages, (May 2011).

* cited by examiner

*Primary Examiner* — Karen Cochrane Carlson
*Assistant Examiner* — Natalie Moss
(74) *Attorney, Agent, or Firm* — Vorys, Sater, Seymour & Pease LLP; Mih Suhn Koh

(57) ABSTRACT

Provided is a composition for preventing or alleviating skin wrinkles containing honeybush (*Cyclopia intermedia*) extract, a fraction thereof, or a fermented honeybush as an active ingredient. More particularly, the honeybush extract or fermented honeybush of the claimed subject matter can reduce the length and depth of skin wrinkles caused by UV irradiation and reduce the thickness of the epidermal layer, in addition to suppress collagen tissue breakdown reactions, indicating it is excellent in alleviating skin wrinkles, so that it can be effectively used as an active ingredient of a composition for preventing or alleviating skin wrinkles.

8 Claims, 3 Drawing Sheets

COMPOSITION FOR PREVENTING OR ALLEVIATING SKIN WRINKLES CONTAINING HONEYBUSH EXTRACT OR FERMENTED HONEYBUSH AS AN ACTIVE INGREDIENT

BACKGROUND OF THE INVENTION

1. Field of the Invention

The present invention relates to a composition for preventing or alleviating skin wrinkles containing honeybush (*Cyclopia intermedia*) extract, the fraction thereof, or fermented honeybush as an active ingredient.

2. Description of the Related Art

As getting old, human skin is also aged and the most representative symptom of skin aging is wrinkle. Wrinkle is a phenomenon showing aging. The major mechanism involved in skin wrinkle formation is explained as follows: When skin is continuously exposed on oxidative stress coming from toxic environment such as air pollution, UV exposure, stress or disease, body radical is increased to destroy collagen, elastin, and hyaluronic acid, which are dermal connective tissues, and thereby settling of a certain part of skin (wrinkle) occurs. Such mechanism can further oxidize lipids in cell membrane, resulting in cell destruction with causing such diseases as dermatitis, acne, and skin cancer.

Cause of wrinkle, according to the structure of skin, is explained in more detail hereinafter. Skin structure is largely composed of epidermis and dermis. Epidermis is a thin protective layer composed of keratinocytes, melanocytes, and Langerhans cells. Dermis is a thicker and more complicated layer composed of connective tissues and fibrous tissues comprising collagen and elastic fibers. Collagen is a major structural protein of skin which is responsible for tensile strength and toughness, while elastic fiber plays an important role in skin resilience and skin elasticity.

When turn-over of keratinocytes is decreased in epidermis, stratum corneum is accumulated and thereby the stratum corneum becomes thicker and loses moisture retaining capacity. So, keratin becomes hardened and as a result wrinkle is generated. The dermoepidermal junction area is importantly involved in epidermal cell support, attachment, nutrients transfer, and regulation of epidermal differentiation. Collagen IV and VII can be decreased by the causes of aging, and particularly by UV. At this time, epidermis and dermis supporting role of collagen is weakened and so is selective transmission function. Then, toxic components can affect dermis easily to cause wrinkles (Keene D R et al., The Journal of Cell Biology 1987 104(3):611-621).

Dermis is the tissue comprising connective tissues down the epidermis, which is not as compact as keratinocytes, the epidermal cells, and has extracellular open space. That is, the dermis is composed of network structure of macromolecules called extracellular matrix. The said extracellular matrix is generated by fibroblasts in the dermis and composed of fibrous proteins such as collagen and elastin and polysaccharides called acid mucopolysaccharides such as hyaluronic acid. The connective tissues involved in skin wrinkle formation are the fibrous components such as collagen fiber, reticular fiber, and elastic fiber. Collagen and elastin are elaborately cooperating in the dermis to maintain skin flexibility and elasticity.

Collagen is the fibrous tissue responsible for skin flexibility, which takes approximately 70% of total dermal tissue. As a major element composing skin, collagen is involved in mechanical rigidity, tissue coherence, cell attachment, and cell differentiation in the dermal layer.

The basic role of skin is to keep moisture from evaporating from human body and to prevent the invasion of foreign toxic materials. Since skin is always exposed on external stimuli, it necessarily has many defense mechanisms. Skin is a kind of expression of beauty. That is, healthy and clear skin is accepted as a sign of beauty. Recently, it is not only women but also men who are interested in skin trouble including skin aging, and therefore skin care products are rush to be developed.

To reduce skin wrinkles, ascorbic acid, α-tocopherol, retinol and its derivatives, and super oxide dismutase (SOD) are included in cosmetics or medicines as a free radical scavenger or a skin wrinkle remover, in order to prevent wrinkles and other skin diseases. However, these materials have disadvantages of high price and chemical instability, which makes them non-practical. Therefore, the development of a material that is safer and more effective in alleviating skin wrinkles has been an important target of study not only in the medicinal and food industry but also in cosmetic industry.

Retinoids used for cosmetic compositions for alleviating skin wrinkles are exemplified by retinol, retinal, retinoic acid, retinyl acetate, retinyl linoleate, and retinyl palmitate, etc. Among them, retinol is an endogenous compound which is essential for the differentiation and growth of epithelial tissue. Compared with such retinoids as retinoic acid, etc, retinol is highly stable, which makes it as an excellent, appropriate raw material of cosmetics for alleviating skin wrinkles.

It has been proved by clinical tests for skin that the said retinoid is effective in alleviating skin wrinkles. However, when it is added in a skin care product, it might cause changes in color and scent of the product. In addition, even with a small dose, it can cause side effects such as skin irritation. Titer reduction caused by changes of the properties and following effectiveness decrease are other problems.

To overcome the said problems of the retinoid, it is required to develop a cosmetic composition for alleviating wrinkles using bioactive materials originated from natural substances. Such bioactive materials are advantageous in the points of less side effects on skin and less chemical changes of the properties, indicating that they are excellent in stability and safety. Therefore, studies have been focused on using medicinal plants for the development of a cosmetic composition for preventing or alleviating skin wrinkles.

Honeybush (*Cyclopia intermedia*) is an evergreen shrub belonging to Melianthaceae, which is only distributed in a narrow area of mountain ridge at east-west seashore in Cape region of South Africa and has a great similarity with Rooibos. The name 'honeybush' is given to *Cyclopia intermedia* because the flower of it smells honey. The way of eating this herb or the effect of it is similar to that of Rooibos, but the taste is much sweeter than Rooibos. Honeybush is processed mainly as a tea. It contains a small amount of tannin but has no caffeine at all. Instead, honeybush contains various minerals (for example, iron, potassium, calcium, copper, zinc, magnesium, etc). It has been used to treat cold, insomnia, and stomachache since long before and known to have blood sugar reducing effect. In the description of PCT/EP2008/052863, anti-diabetic effect of honeybush extract is described. According to a previous report, honeybush extract can control the differentiation of esophageal papilloma (Sissing L et al., Nutrition and cancer 2011 63(4):600-610). However, it is still unknown whether or not honeybush extract has the effect of alleviating skin wrinkles.

The present inventors studied to develop natural plant extracts to alleviate skin wrinkles. As a result, the present inventors confirmed that the honeybush extract or fermented honeybush could reduce the length and depth of skin wrinkles caused by UV irradiation and reduce the thickness of the epidermal layer, in addition to suppress collagen tissue breakdown reaction, suggesting skin wrinkle alleviating effect. Accordingly, the present inventors completed this invention by confirming that the honeybush extract or fermented honeybush could be effectively used as an active ingredient of a composition for preventing or alleviating skin wrinkles.

SUMMARY OF THE INVENTION

It is an object of the present invention to provide a composition for preventing or alleviating skin wrinkles containing honeybush (*Cyclopia intermedia*) extract, the fraction thereof, or fermented honeybush as an active ingredient.

It is another object of the present invention to provide a prevention method for skin wrinkles containing the step of administering the honeybush extract, the fraction thereof, or fermented honeybush to a subject.

It is also an object of the present invention to provide an alleviation method for skin wrinkles containing the step of administering the honeybush extract, the fraction thereof, or fermented honeybush to a subject having skin wrinkles.

In addition, it is an object of the present invention to provide a use of the honeybush extract, the fraction thereof, or fermented honeybush for the preparation of a composition for preventing or alleviating skin wrinkles.

To achieve the above object, the present invention provides a cosmetic composition for preventing or alleviating skin wrinkles containing the honeybush (*Cyclopia intermedia*) extract, the fraction thereof, or fermented honeybush as an active ingredient.

The present invention also provides a skin external preparation for preventing or alleviating skin wrinkles containing the honeybush extract, the fraction thereof, or fermented honeybush as an active ingredient.

The present invention further provides a pharmaceutical composition for preventing or alleviating skin wrinkles containing the honeybush extract, the fraction thereof, or fermented honeybush as an active ingredient.

The present invention also provides a health food for preventing or alleviating skin wrinkles containing the honeybush extract, the fraction thereof, or fermented honeybush as an active ingredient.

The present invention also provides a prevention method of skin wrinkles containing the step of administering the honeybush extract, the fraction thereof, or fermented honeybush to a subject.

The present invention also provides an alleviation method for skin wrinkles containing the step of administering the honeybush extract, the fraction thereof, or fermented honeybush to a subject having skin wrinkles.

The present invention also provides a use of the honeybush extract, the fraction thereof, or fermented honeybush for the preparation of a cosmetic composition for preventing or alleviating skin wrinkles.

The present invention also provides a use of the honeybush extract, the fraction thereof, or fermented honeybush for the preparation of a skin external preparation for preventing or alleviating skin wrinkles.

The present invention also provides a use of the honeybush extract, the fraction thereof, or fermented honeybush for the preparation of a pharmaceutical composition for preventing or alleviating skin wrinkles.

In addition, the present invention provides a use of the honeybush extract, the fraction thereof, or fermented honeybush for the preparation of a health food for preventing or alleviating skin wrinkles.

ADVANTAGEOUS EFFECT

As explained hereinbefore, the honey bush extract or fermented honeybush of the present invention can reduce the length and depth of skin wrinkles caused by UV irradiation and reduce the thickness of the epidermal layer, in addition to suppress collagen tissue breakdown reactions, indicating it is excellent in alleviating skin wrinkles, so that it can be effectively used as an active ingredient of a composition for preventing or alleviating skin wrinkles.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
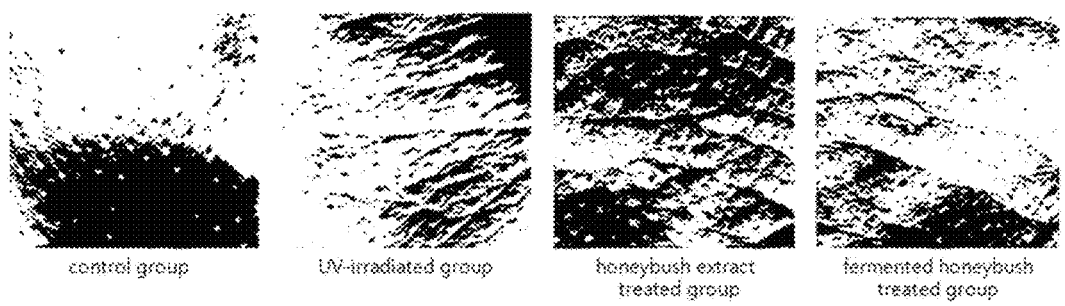
FIG. 1 illustrates the alleviating effect of the honeybush extract or fermented honeybush on skin wrinkles, confirmed by replica analysis.

Hereinafter, the present invention is described in detail.

The present invention provides a cosmetic composition for preventing or alleviating skin wrinkles containing the honeybush (*Cyclopia intermedia*) extract, the fraction thereof, or fermented honeybush as an active ingredient.

The honeybush extract of the present invention is preferably prepared by the method comprising the following steps, but not always limited thereto:

1) extracting honeybush by adding an extraction solvent;
2) cooling and filtering the extract obtained in step 1);
3) concentrating the extract filtered in step 2) under reduced pressure; and
4) preparing dried powder with the extract concentrated in step 3).

In the above method, the honeybush of step 1) is either obtained by cultivation or purchased. Any part of honeybush can be used but leaves, seed, fruits, roots, or aerial parts thereof are preferably used, but not always limited thereto.

The said extraction solvent is preferably selected from the group consisting of water, $C_1$~$C_2$ lower alcohol, methanol, hexane, acetone, ethyl acetate, saturated normal butane, chloroform, methylene chloride, and a mixed solvent thereof, but not always limited thereto. The alcohol herein is preferably $C_1$~$C_2$ lower alcohol, and the lower alcohol is preferably ethanol or methanol. Water is more preferred as an extraction solvent, but not always limited thereto.

The extraction method is preferably shaking extraction, or reflux extraction, and cold reflux extraction is more preferred, but not always limited thereto. The extraction solvent is preferably added to honeybush 2~10 times the volume of honey bush, and more preferably 5~10 times, and most preferably 10 times the volume of honeybush, but not always limited thereto. The extraction temperature is preferably room temperature ~100° C., but not always limited thereto. The extraction time is 1~3 hours, and more preferably 1 hour, but not always limited thereto. The extraction is preferably repeated 1~3 times, and more preferably repeated 2 times, but not always limited thereto.

In this method, concentration under reduced pressure in step 3) is preferably performed by using a vacuum concentrator or a vacuum rotary evaporator, but not always limited thereto. Drying in step 4) is preferably performed by reduced-pressurized drying, vacuum drying, boiling drying, spray drying, or freeze drying, but not always limited thereto.

The fraction of the honeybush extract is obtained by fractionation of the extract obtained above and at this time the solvent used for the fractionation is selected from the group consisting of water, $C_1$~$C_2$ lower alcohol, methanol, hexane, acetone, ethyl acetate, saturated normal butanol, chloroform, methylene chloride, and a mixed solvent thereof, but not always limited thereto.

The fermented honeybush is preferably prepared by the method comprising the following steps, but not always limited thereto:

1) inoculating animal milk with lactic acid bacteria;
2) mixing the inoculated milk of step 1) with a carbon source and the honeybush extract or the fraction thereof; and
3) fermenting the mixture of step 2).

The lactic acid bacteria of step 1) is preferably *Streptococcus thermophilus*, but not always limited thereto and in fact any lactic acid bacteria possibly used for fermentation can be used herein.

The lactic acid bacteria of step 1) is preferably cultured in MRS (de Man, Rogosa & Sharpe), but not always limited thereto and in fact any medium usable for the culture of lactic acid bacteria can be used herein.

The lactic acid bacteria of step 1) is preferably inoculated at the density of $3\times10^4$~$3\times10^6$ CFU/ml, and more preferably at the density of $3\times10^5$ CFU/ml, but not always limited thereto.

The carbon source of step 2) is preferably glucose or sugar, but not always limited thereto.

The honeybush extract or the fraction thereof of step 2) is preferably added at the ratio of 3~10% (v/v), and more preferably at the ratio of 5~6% (v/v), and most preferably at the ratio of 5% (v/v), but not always limited thereto. The fermentation in step 3) is preferably performed in a 35~38° C. incubator for 1~3 days, and more preferably in a 37~38° C. incubator for 1 day, but not always limited thereto.

In a preferred embodiment of the present invention, the honeybush extract or fermented honeybush reduced the length and depth of skin wrinkles caused by UV irradiation, reduced the thickness of the epidermal layer, and inhibited collagen breakdown reactions, indicating skin wrinkle alleviation effect, so that it can be effectively used for a cosmetic composition for preventing or alleviating skin wrinkles (see FIG. 1~FIG. 6).

The cosmetic composition can be provided in the form of solution, gel, solid or dough anhydride, emulsion prepared by dispersing oil phase on water phase, suspension, microemulsion, microcapsule, microgranule, ionic (liposome) or non-ionic vesicle, cream, skin, lotion powder, spray, and conceal stick. In addition, the cosmetic composition can be formulated as an aerosol composition containing a foam or compressed propellant.

The cosmetic composition can include, in addition to the honeybush extract, the fraction thereof, or fermented honeybush of the present invention, a supplement generally used in the field of cosmetics such as fatty substance, organic solvent, resolvent, concentrate, gelling agent, softener, antioxidant, suspending agent, stabilizer, foaming agent, odorant, surfactant, water, ionic or non-ionic emulsifying agent, filler, sequestering agent, chelating agent, preserving agent, vitamin, blocker, moisturing agent, essential oil, dye, pigment, hydrophilic or hydrophobic activator, lipid vesicle or other components generally used in cosmetics.

In a preferred embodiment of the present invention, the content of the extract of the present invention in the cosmetic composition containing the honeybush extract, the fraction thereof, or fermented honeybush of the present invention is 1~15 weight % by the total weight of the composition, and preferably 2~10 weight %.

The skin external preparation containing the honeybush extract, the fraction thereof, or fermented honeybush of the present invention can additionally include a supplement generally used in the field of skin science such as fatty substance, organic solvent, resolvent, concentrate, gelling agent, softener, antioxidant, suspending agent, stabilizer, foaming agent, odorant, surfactant, water, ionic or non-ionic emulsifying agent, filler, sequestering agent, chelating agent, preserving agent, vitamin, blocker, moisturing agent, essential oil, dye, pigment, hydrophilic or hydrophobic activator, lipid vesicle or other components generally used in a skin external preparation. The amount of the above supplement can be determined as generally accepted in the field of skin science.

The cosmetic composition for preventing or alleviating skin wrinkles of the present invention can include general anti-wrinkle agents in addition to the said honeybush extract, the fraction thereof, or fermented honeybush. When an additional ingredient that is helpful for skin health care is added, the preventing or alleviating effect of the composition of the invention on skin wrinkles is expected to increase more but safety on skin, easiness of formulation, and stability of active ingredients have to be considered as well. The additional anti-wrinkle agent addable to the composition of the present invention is those functional materials notified by Ministry of Food and Drug Safety which are exemplified by retinol, retinyl palmitate, adenosine, polyethoxylated retinamide, collagen, and animal placenta originated proteins, etc, but not always limited thereto. The additional anti-wrinkle agent can be included at the ratio of 0.0001~10 weight %. At this time, the weight % is regulated by considering the activity of collagen synthesis or collagenase inhibition, and skin safety matters, etc.

The present invention also provides a skin external preparation for preventing or alleviating skin wrinkles comprising the honeybush extract, the fraction thereof, or fermented honeybush as an active ingredient.

The honeybush extract, the fraction thereof, or fermented honeybush can be mixed with a skin external preparation as it is or if necessary in the form of an additive prepared by mixing one or two or more pharmaceutically acceptable ingredients. The pharmaceutically acceptable ingredient usable for a skin external preparation in this invention is exemplified by reducing sugar, non-reducing sugar, sugar alcohol, soluble polysaccharide, synthetic polymer, antioxidant, and emulsifier, but not always limited thereto. More particularly, sugar derivatives of α,α-trehalose, α-glucosyl α,α-trehalose, α-maltosyl α,α-trehalose, and α-maltotriosyl α,α-trehalose and carbohydrates comprising the sugar derivatives (referred as 「sugar derivative of α, α-trehalose」 hereinafter) described in Japanese Patent No. H07-143876 and 3182679 have strong activity to inhibit degradation of vitamin glycoside, to prevent consolidation, and to inhibit moisture absorption, making them more preferable candidates. These ingredients for a skin external preparation are advantageous when they are added in the honeybush extract, the fraction thereof, or fermented honeybush of the present invention because they can prevent malfunction or consolidation of the same during the preservation or transportation.

The mixing ratio of such additive for a skin external preparation to the honeybush extract, the fraction thereof, or fermented honeybush of the present invention or the skin external preparation containing the same is not limited as long as it does not arrest the function or effect of the same. However, considering the expected function and convenience in use, the concentration of the additive is preferably 0.01~20%, more preferably 0.1~10%, and most preferably 0.5~10% by the total weight of the skin external preparation.

The additive for a skin external preparation can be added to the honeybush extract, the fraction thereof, or fermented honeybush of the present invention or the skin external preparation containing the same at any time during the process of the skin external preparation of the invention from the raw material stage to the final product stage. At this time, any method selected from the group consisting of mixing, dissolution, melting, dispersion, suspending, emulsification, reverse micellization, infiltration, crystal eduction, spraying, spreading, nebulization, injection, soaking, and consolidation can be properly used. These methods can be used alone or as a combination of at least two methods.

The skin external preparation in this invention includes cosmetics, quasi drugs, and medicines for skin, and also includes chemical products, industrial products, and miscellaneous goods possibly contacted on skin. The formulation of the skin external preparation is not limited and solution system, microemulsion system, emulsion system, powder dispersive system, water-oil 2 phase system, water-powder 2 phase system, and water-oil-powder 3 phase system are all accepted. The use of the honeybush extract or fermented honeybush of the present invention is also not limited. For example, the honeybush extract or fermented honeybush of the present invention can be used for the preparation of basic cosmetics, finishing cosmetics, skin cosmetics, cleansing cosmetics, facial cleansers, skin lotions, creams, milky lotions, packs, foundations, white powders, powders, lipsticks, eye shadows, perfumes, bathing cosmetics, oral cosmetics, suntan/sunscreen lotions, make-up cosmetics, nail cosmetics, eyeliner cosmetics, lip cosmetics, oral cosmetics, facial cosmetics, cosmetic oils, aromatic cosmetics, body cosmetics, hair cosmetics, hair washing cosmetics, cosmetic soaps, medicinal soaps, toothpastes, mouth washers, deodorants, hair nourishers, shaving cosmetics, sunblocks, antipruritics, cleaning agents, sanitizers, disinfectants, discoloring agents, and hair removers in the forms of skin water, lotion, milky lotion, cream, ointment, suspension, emulsion, paste, mousse, cosmetic, solid, semi-solid, powder, solid powder, jelly, gel, aerosol, spray, roche, pack, and face mask. The honeybush extract or fermented honeybush of the present invention can also be used for the preparation of preventive or therapeutic agents for various diseases such as athlete's foot, hemorrhoid, acne, wound, burn, frostbite, lacquer induced dermatitis, sore, inflammation, infection, allergy, atopy, ulcer, and tumor.

Particularly, the honeybush extract or fermented honeybush of the present invention can be used for the preparation of cosmetic soap, cleansing cream, cleansing foam, cleansing milk, cleansing lotion, cleansing oil, massage cream, cold cream, moisture cream, vanishing cream, hand cream, moisture lotion, cosmetic oil, liquid foundation, powder foundation, cake foundation, stick foundation, oily compact foundation, cream foundation, cheek brush, emulsion foundation, basic cosmetics, body powder, cream powder, white powder, liquid powder, solid powder, kneaded powder, talcom powder, rouge shadow, baby powder, cheek rouge, eye brow paint, mascara, lipstick, lip cream, pack, shaving cream, after shaving cream, lotion, hand lotion, shaving, lotion, after shaving lotion, suntan cream, suntan oil, sunscreen lotion, suntan lotion, emollient toilet water, astringent, cleansing toilet water, shake lotion, facial shampoo, body shampoo, hair shampoo, cleansing powder, hand soap, facial rinse, body rinse, hair rinse, hair treatment, hair tonic, hair growth cosmetic, pomade, hair cream, hair liquid, hair tonic, set lotion, easy comb oil, hair oil, hair spray, hair mousse, hair dye, hair bleach, color rinse, color spray, permanent wave solution, press powder, loose powder, eye cream, eye shadow, cream eye shadow, powder eye shadow, eye liner, eye brow pencil, mascara, hair removing cream, general perfume, powder perfume, eau de cologne, deodorant, bath agent, bath oil, bath salt, cosmetic oil, baby oil, nail color, enamel, enamel remover, nail treatment, mouth wash, toothpaste, powder toothpaste, insect repeller (insect remover), ointment for curing external wound, anti-microbial cream, steroid ointment, sheet or film type puff applied on the affected area of skin or oral cavity, detergent or soap for clothes, floor detergent, kitchen cleaner, and cleanser, etc.

The present invention further provides a pharmaceutical composition for preventing or alleviating skin wrinkles containing the honeybush extract, the fraction thereof, or fermented honeybush as an active ingredient.

The present invention also provides a prevention method of skin wrinkles containing the step of administering the honeybush extract, the fraction thereof, or fermented honeybush to a subject.

The present invention also provides an alleviation method for skin wrinkles containing the step of administering the honeybush extract, the fraction thereof, or fermented honeybush to a subject having skin wrinkles.

The honeybush extract or fermented honeybush of the present invention reduced the length and depth of skin wrinkles caused by UV irradiation, reduced the thickness of the epidermal layer, and inhibited collagen breakdown reactions, suggesting excellent skin wrinkle alleviation effect, so that it can be effectively used as a pharmaceutical composition for preventing or alleviating skin wrinkles.

The pharmaceutical composition of the present invention can additionally include generally used excipients, disintegrating agents, sweetening agents, lubricants, and flavors, etc. The composition of the present invention can be formulated as tablets, capsules, powders, granules, suspensions, emulsions, syrups, and other liquid formulations.

Particularly, the formulations of the pharmaceutical composition of the present invention for oral administration are exemplified by tablets, troches, lozenges, soluble or oil-based suspensions, powders or granules, emulsions, hard or soft capsules, syrups, and elixirs, etc. When the pharmaceutical composition of the present invention is formulated as tablets and capsules, binding agents such as lactose, saccharose, sorbitol, mannitol, starch, amylopectin, cellulose or gelatin, excipients like dicalcium phosphate, disintegrating agents such as corn starch or sweet potato starch, and lubricants such as magnesium stearate, calcium stearate, sodium stearyl fumarate or polyethyleneglycol wax are included. In the case of capsules, liquid carriers like fatty oil is additionally included.

The pharmaceutical composition of the present invention can be administered by orally or parenterally and the parenteral administration includes subcutaneous injection, intravenous injection, intramuscular injection and intrathoracic injection. To prepare the pharmaceutical composition of the present invention as a formulation for parenteral administration, the honeybush extract, the fraction thereof, or fermented honeybush of the present invention is mixed with a stabilizer or a buffering agent in water to produce a suspension, which is then formulated as ampoules or vials.

The pharmaceutical composition of the present invention is preferably treated by transdermal administration, and more preferably treated by topical application, but not always limited thereto.

The effective dosage of the composition of the present invention can be determined according to absorptiveness of the active ingredient, inactivation rate, excretion rate, age, gender, health condition and severity of a disease by those in the art. In the case of oral administration, the pharmaceutical composition of the present invention can be administered by 0.01~500 mg/kg per day for an adult, and more preferably by 1~100 mg/kg per day. The administration frequency is once a day or a few times a day. The dosage cannot limit the scope of the present invention by any means. The skin external preparation of the present invention is preferably applied at the dosage of 0.5 ml~5.0 ml/day/adult, 1~5 times a day, for at least 1 month.

The present invention also provides a health food for preventing or alleviating skin wrinkles containing the honeybush extract, the fraction thereof, or fermented honeybush as an active ingredient.

The honeybush extract or fermented honeybush of the present invention reduced the length and depth of skin wrinkles caused by UV irradiation, reduced the thickness of the epidermal layer, and inhibited collagen breakdown reactions, suggesting excellent skin wrinkle alleviation effect, so that it can be effectively used for a health food for preventing or alleviating skin wrinkles.

The honeybush extract, the fraction thereof or fermented honeybush of the present invention can be used as food additive. In that case, the honeybush extract, the fraction thereof or fermented honeybush can be added as it is or as mixed with other food components according to the conventional method.

The food herein is not limited. For example, the honeybush extract, the fraction thereof or fermented honeybush of the present invention can be added to caramels, meats, sausages, breads, chocolates, candies, snacks, cookies, pizza, ramyuns, noodles, gums, dairy products including ice cream, soups, beverages, tea, drinks, alcoholic drinks and vitamin complex, etc, and in wide sense, almost every food applicable in the production of health food can be included.

The composition for health beverages of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and glucose alcohols such as xilytole, sorbitol and erythritol. Besides, natural sweetening agents such as thaumatin and stevia extract, and synthetic sweetening agents such as saccharin and aspartame can be included as a sweetening agent. The content of the natural carbohydrate is preferably 0.01~0.04 g and more preferably 0.02~0.03 g in 100 ml of the composition.

In addition to the ingredients mentioned above, the honeybush extract, the fraction thereof or fermented honeybush of the present invention can include a variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, carbonators which used to be added to soda, etc. The honeybush extract, the fraction thereof or fermented honeybush of the present invention can also include fruit flesh addable to natural fruit juice, fruit beverages and vegetable beverages. All the mentioned ingredients can be added singly or together. The mixing ratio of those ingredients does not matter in fact, but in general, each can be added by 0.01~0.1 weight part per 100 weight part of the honeybush extract, the fraction thereof or fermented honeybush of the present invention.

The health food for preventing or alleviating skin wrinkles of the present invention can include general anti-wrinkle agents in addition to the said honeybush extract, the fraction thereof, or fermented honeybush. When an additional ingredient that is helpful for skin health care is added, the preventing or alleviating effect of the health food of the invention on skin wrinkles is expected to increase more but safety on skin, easiness of formulation, and stability of active ingredients have to be considered as well. The additional anti-wrinkle agent addable to the health food of the present invention is those functional materials notified by Ministry of Food and Drug Safety which are exemplified by chlorella, spirulina, N-acetylglucosamine, and aloe gel, etc, but not always limited thereto. The additional anti-wrinkle agent can be included at the ratio of 0.0001~10 weight %. At this time, the weight % is regulated by considering the activity of collagen synthesis or collagenase inhibition, and skin safety matters, etc.

The present invention also provides a use of the honeybush extract, the fraction thereof, or fermented honeybush for the preparation of a cosmetic composition for preventing or alleviating skin wrinkles.

The present invention also provides a use of the honey bush extract, the fraction thereof, or fermented honeybush for the preparation of a skin external preparation for preventing or alleviating skin wrinkles.

The present invention also provides a use of the honeybush extract, the fraction thereof, or fermented honeybush for the preparation of a pharmaceutical composition for preventing or alleviating skin wrinkles.

In addition, the present invention provides a use of the honeybush extract, the fraction thereof, or fermented honeybush for the preparation of a health food for preventing or alleviating skin wrinkles.

The honeybush extract or fermented honeybush of the present invention reduced the length and depth of skin wrinkles caused by UV irradiation, reduced the thickness of the epidermal layer, and inhibited collagen breakdown reactions, suggesting excellent skin wrinkle alleviation effect, so that it can be effectively used for a method for preventing or alleviating skin wrinkles and for a composition preventing or alleviating skin wrinkles.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

EXAMPLE 1

Preparation of Honeybush Extract

Honeybush was purchased from Renewallife (http://www.renewallife.com). The purchased sample was stored in a refrigerator for oriental medicine wherein the temperature was maintained at 5.5±0.3° C. and the humidity was maintained at 50±5%. 220 ml of water was added to 25g of honeybush (total weight), followed by reflux cold extraction twice, for one hour each. As a result, honeybush extract was obtained. The prepared extract was filtered with a filter paper and the obtained filtrate was loaded in a vacuum concentrator to remove the solvent. As a result, 4.3 g of the honeybush extract of the present was obtained.

EXAMPLE 2

Preparation of Fermented Honeybush

To prepare the fermented honeybush of the present invention, 1 mL of lactic acid bacteria (Streptococcus thermophilus, $3\times10^5$ CFU/ml) cultured in MRS (de Man, Rogosa, & Sharpe) medium was inoculated in 100 mL of animal milk (white milk). 3 g of sugar and the honeybush extract prepared in Example 1 was added to the inoculated milk (5%, w/v). Then, the mixture was fermented in a 37□ incubator for 1 day. As a result, 100 g of the fermented honeybush of the present invention was obtained.

EXPERIMENTAL EXAMPLE 1

Evaluation of Wrinkle Alleviation Effect of the Honeybush Extract or Fermented Honeybush by Replica Analysis Replica analysis was performed to evaluate wrinkle alleviation effect of the honeybush extract or fermented honeybush of the present invention.

<1-1> Test Animal and Sample Treatment

Male HR-1 hairless mice (Japan SLC, Inc.) at 7 weeks were used as test animals. The mice were purchased from Central Lab. Animal Inc., and adapted to the environment for 1 week before being used. During the period of adaptation, general conditions of the mice were observed to select healthy mice for the experiment. The environmental conditions were as follows; temperature: 23±3° C., relative humidity: 50±5%, light/dark cycle: 12/12 hour (turn on at 7:00 and turn off at 19:00). The test animals were distributed in polycarbonate cage (200×320×450 mm, Three-shine Co., Daejeon, Korea), 5 mice/cage. Mouse exclusive feeds (5L79, Charles river, USA) and UV-sterilized water were provided freely.

As shown in Table 1, experiment was performed with 4 groups, the control group (control), the UV-irradiated group (UV), the honeybush extract treated group (HB), and the fermented honeybush treated group (STC HB). The test sample was orally administered to the mice by using a mouse zonde for 8 weeks, 5 days a week.

TABLE 1

| UV irradiation and dosage | | |
|---|---|---|
| Experimental Group | UV | Dosage |
| Control group | x | — |
| UV-irradiated group | o | UV-sterilized water: 5 ml/kg |
| Honeybush extract treated group (HB) | o | 100 mg/kg |
| Fermented honeybush treated group (STC HB) | o | 5 ml/kg |

<1-2> UV Irradiation

The experimental groups were irradiated with UV for 8 weeks, three times a week, except the control group. UV irradiation was performed by using an UVB lamp (Mineralight UV Display lamp, UVP, USA). UV dosage was 60 $mJ/cm^2$ for week 1~week 2, 90 $mJ/cm^2$ for week 3~week 5, and 120 $mJ/cm^2$ for week 6~week 8. The UV dosage was controlled by regulating irradiation hours after measuring the intensity of radiation by using an optical measuring instrument (Delta OHM, Italy).

<1-3> Evaluation of Wrinkle Alleviation Effect by Replica Analysis

To measure the wrinkle alleviation effect of the honeybush extract or fermented honeybush of the present invention, replica was made on the back skin of each hairless mouse of Experimental Example <1-1> by using silicon rubber, followed by observation of wrinkle formation.

Particularly, replica was prepared by using Repliflo Cartridge Kit (CuDerm Corporation, USA), which was then applied thinly onto the back of the mouse. After complete drying, the disc was taken apart carefully to prepare replica. The replica preparation was performed at 20~22° C. with 40~50% humidity.

As a result, as shown in FIG. 1, thick and deep wrinkles were formed along with fine wrinkles in the UV irradiated group, compared with the normal control group. In the honeybush extract treated group or the fermented honeybush treated group, the thickness or depth of wrinkles caused by UV irradiation was alleviated (FIG. 1).

In addition, the alleviation of thick wrinkles was more peculiar in the fermented honeybush treated group than in the UV irradiated group. This alleviation effect in the fermented honeybush treated group was also greater than that of the honeybush extract treated group. So, the thick wrinkles became thinner almost close to those of the normal control group.

Therefore, it was confirmed that the honeybush extract or fermented honeybush of the present invention had excellent alleviation effect on skin wrinkles caused by UV irradiation.

<1-4> Evaluation of Wrinkle Alleviation Effect by Investigating the Length and Depth of Wrinkles To analyze quantitatively the wrinkle alleviation effect of the honeybush extract or fermented honeybush of the present invention, the length and depth of wrinkles were investigated.

Particularly, the replica prepared in Experimental Example <1-3> was used to measure the length and depth of wrinkles by using Visioline VL650. The replica was inserted in the standard cartridge designed to let a specific light source pass through. Then, the light source was pass through at 35° of incidence angle. Shadow intensity images generated according to the thickness of the replica were filed by using CCD camera. Then, the length and depth of wrinkles were measured by using Skin Visiometer VL650 software. The obtained results were analyzed by one-way ANOVA and Student t-test to evaluate the statistic significance between the control and the experimental groups ($p<0.05$).

Figure 2:
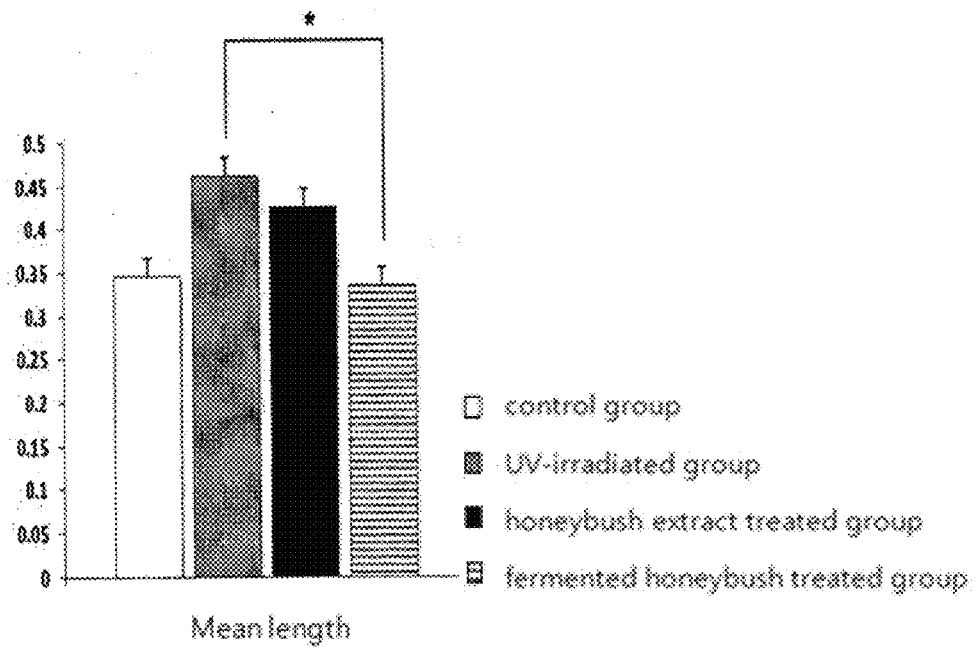
FIG. 2 illustrates the alleviating effect of the honeybush extract or fermented honeybush on skin wrinkles, confirmed by analysis of the mean length of wrinkles.

As a result, as shown in FIG. 2, the length of wrinkles was increased in the UV irradiated group, compared with that in the control group. In the meantime, the length of wrinkles in the honeybush extract treated group was decreased 0.89% by that in the UV irradiated group. The length of wrinkles in the fermented honeybush treated group was decreased 28% by that in the UV irradiated group. These results were statistically significant ($p<0.05$) (FIG. 2).

Figure 3:
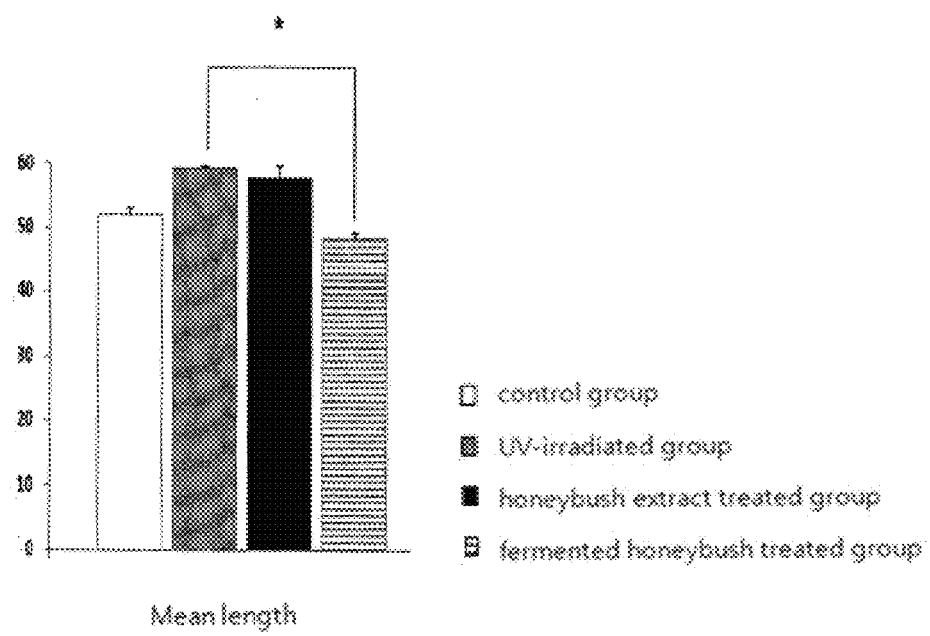
FIG. 3 illustrates the alleviating effect of the honeybush extract or fermented honeybush on skin wrinkles, confirmed by analysis of the mean depth of wrinkles.

As shown in FIG. 3, the depth of wrinkles was increased in the UV irradiated group, compared with that in the control group. In the meantime, the depth of wrinkles in the fermented honeybush treated group was decreased 17% by that in the UV irradiated group, which was also statistically significant ($p<0.05$) (FIG. 3).

From the above results, it was confirmed that the honeybush extract or fermented honeybush of the present invention had suppressive effect on skin wrinkles caused by UV irradiation, and the suppressive effect of the fermented honeybush was greater than that of the honeybush extract.

EXPERIMENTAL EXAMPLE 2

Evaluation of Wrinkle Alleviation Effect by Histological Staining

To confirm the wrinkle alleviation effect of the honeybush extract or fermented honeybush of the present invention via histological observation of skin, skin tissues were taken from the hairless mice, followed by histological staining.

Particularly, skin tissues were taken from each hairless mouse of Experimental Example <1-1>, which were fixed in 10% neutral formalin solution. The fixed tissues were washed, dehydrated, cleaned, infiltrated, and embedded in paraffin according to the conventional method. The paraffin block was made into 4 um thick sections, followed by Hematoxylin & Eosin (H&E) staining and Masson's trichome staining.

Figure 4:
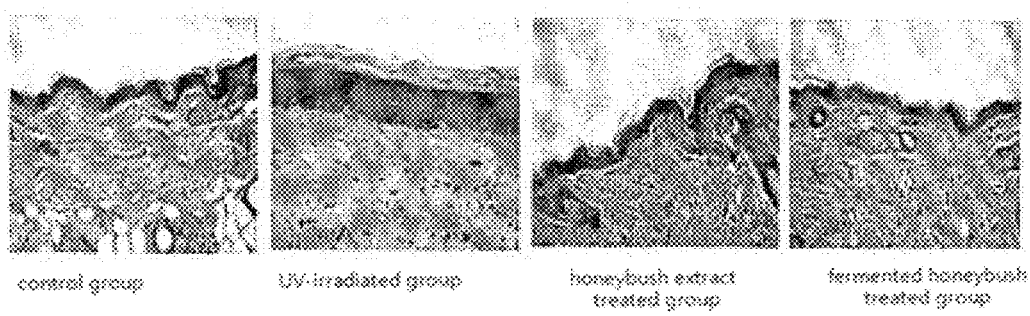
FIG. 4 illustrates the alleviating effect of the honeybush extract or fermented honeybush on skin wrinkles, confirmed by Hematoxylin & Eosin (H&E) staining.

As a result, as shown in FIG. 4, it was confirmed by H&E staining that the stratum corneum was increased in the UV irradiated group, which was more peculiar than in the control group, and the epidermal thickness was also increased. In the meantime, the stratum corneum was alleviated in the honeybush extract treated group and in the fermented honeybush treated group, and the epidermal thickness was reduced (FIG. 4).

Figure 5:
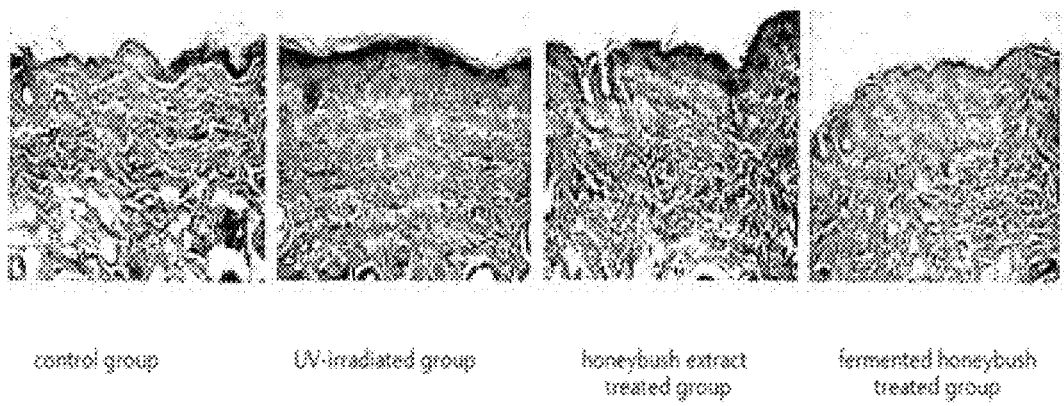
FIG. 5 illustrates the alleviating effect of the honeybush extract or fermented honeybush on skin wrinkles, confirmed by Masson's trichome staining.

As shown in FIG. 5, it was confirmed by Masson's trichome staining that the stratum corneum was hardly observed and the epidermal layer was not thick in the control group. Most of tissue was the dermal layer, in which collagen was distributed regularly. On the other hand, the stratum corneum was thick and collagen was not observed in the UV irradiated group. In the honeybush extract treated group and in the fermented honeybush treated group, collagen fibers were increased, compared with the UV irradiated group (FIG. 5).

In addition, it was confirmed by both histological staining assays that the effects of reducing the stratum corneum and the epidermal thickness and increasing collagen fiber were greater in the fermented honeybush treated group than in the honeybush extract treated group.

From the above results, it was confirmed that the honeybush extract or fermented honeybush of the present invention had alleviation effect on skin wrinkles caused by UV irradiation, and the alleviation effect of the fermented honeybush was greater than that of the honeybush extract.

EXPERIMENTAL EXAMPLE 3

Evaluation of Wrinkle Alleviation Effect by Observing the Changes of Epidermal Thickness The wrinkle alleviation effect of the honeybush extract and fermented honeybush of the present invention was investigated by measuring the changes of epidermal thickness.

Particularly, to measure the epidermal thickness, the distance from the keratin layer to the epidermal basement membrane in the tissue stained with H&E in <Experimental Example 2> was measured by using the special ruler equipped in a microscope. The significance of the obtained results for the control and the experimental groups was evaluated by one-way ANOVA and Student t-test ($p<0.05$). The obtained results were analyzed by one-way ANOVA and Student t-test to evaluate the statistic significance between the control and the experimental groups ($p<0.05$).

Figure 6:
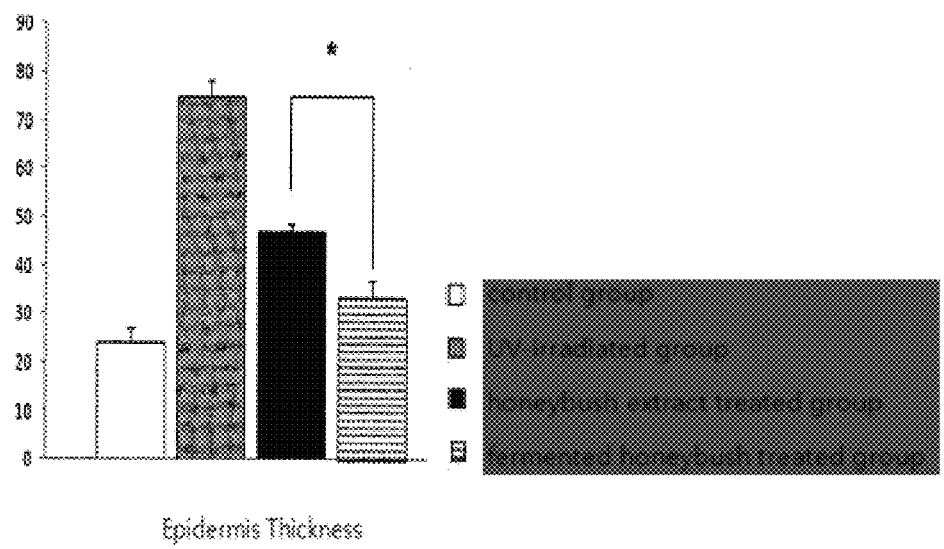
FIG. 6 illustrates the alleviating effect of the honeybush extract or fermented honeybush on skin wrinkles, confirmed by measuring the changes of epidermal thickness.

As a result, as shown in FIG. 6, the epidermal thickness was increased in the UV irradiated group, compared with that in the control group. In the meantime, the epidermal thickness in the honeybush extract treated group was reduced 40% by the UV irradiated group, and the epidermal thickness in the fermented honeybush treated group was significantly reduced 56% by the UV irradiated group (FIG. 6).

This alleviation effect in the fermented honeybush treated group was greater than that of the honeybush extract treated ($p<0.05$).

Therefore, it was confirmed that the honeybush extract and fermented honeybush of the present invention significantly reduced the epidermal thickness, suggesting that they are effective in alleviating skin wrinkles. At this time, the fermented honeybush was more effective than the honeybush extract.

MANUFACTURING EXAMPLE 1

Preparation of Cosmetics Containing the Honeybush Extract or Fermented Honeybush as an Active Ingredient <1-1> Preparation of Emollient Toilet Water Emollient toilet water containing the honeybush extract or fermented honeybush of the present invention as an active ingredient was prepared according to the composition shown in [Table 2].

TABLE 2

| Constituent | Content (weight part) |
| --- | --- |
| Honeybush extract or fermented honeybush | 10.00 |
| 1,3-butyleneglycol | 1.00 |
| EDTA-2Na | 0.05 |
| Allantoin | 0.10 |
| Dipotassium glycyrrhizate | 0.05 |
| Citric acid | 0.01 |
| Sodium citrate | 0.02 |

TABLE 2-continued

| Constituent | Content (weight part) |
|---|---|
| Glycereth-26 | 1.00 |
| Arbutin | 2.00 |
| Hydrogenated castor oil | 1.00 |
| Ethanol | 30.00 |
| Preservative | Small amount |
| Colorant | Small amount |
| Flavor | Small amount |
| Purified water | Proper amount |

<1-2> Preparation of Nutritive Cream

Nutritive cream containing the honeybush extract or fermented honeybush of the present invention as an active ingredient was prepared according to the composition shown in [Table 3].

TABLE 3

| Constituent | Content (weight part) |
|---|---|
| Honeybush extract or fermented honeybush | 10.0 |
| 1,3-butyleneglycol | 7.0 |
| Glycerin | 1.0 |
| D-panthenol | 0.1 |
| Plant extract | 3.2 |
| Magnesium aluminum silicate | 0.3 |
| PEG-40 stearate | 1.2 |
| Stearic acid | 2.0 |
| Polysorbate 60 | 1.5 |
| Glyceryl stearate, lipophilic | 2.0 |
| Sorbitan sesquioleate | 1.5 |
| Cetearyl alcohol | 3.0 |
| Mineral oil | 4.0 |
| Squalane | 3.8 |
| Capric/caprylic triglyceride | 2.8 |
| Vegetable oil | 1.8 |
| Dimethicone | 0.4 |
| Dipotassium glycyrrhizate | Small amount |
| Allantoin | Small amount |
| Sodium hyaluronate | Small amount |
| Tocopheryl acetate | Proper amount |
| Triethanolamine | Proper amount |
| Preservative | Proper amount |
| Flavor | Proper amount |
| Purified water | Proper amount |

<1-3> Preparation of Essence

TABLE 4

| | | Constituent | Content (weight part) |
|---|---|---|---|
| Water phase | 1 | Purified water | 70.58 |
| | 2 | Honeybush extract or fermented honeybush | 8.00 |
| | 3 | Methyl paraben | 0.15 |
| | 4 | Hyaluronic acid extract | 2.50 |
| | 5 | Glycerin | 8.00 |
| Oil phase | 6 | Propyl paraben | 0.10 |
| | 7 | Lecithin | 0.60 |
| | 8 | Macadamia nut oil | 10.0 |
| Additive | 9 | Flavor | 0.07 |

According to the composition ratio shown in [Table 4], purified water, honeybush extract or fermented honeybush, methyl paraben, hyaluronic acid extract, and glycerin were measured and mixed at 80±2° C. to prepare water phase. Propyl paraben, lecithin, and macadamia nut oil were also measure and mixed at 80±2° C. to prepare oil phase.

The oil phase was added to the water phase, followed by mixing to make a mixture in the form of emulsion. Flavor was added to the mixture, followed by cooling down to 35° C. As a result, essence containing the honeybush extract or fermented honeybush of the present invention as an active ingredient was prepared.

MANUFACTURING EXAMPLE 2

Preparation of Pharmaceutical Formulations Containing the Honeybush Extract or Fermented Honeybush as an Active Ingredient <2-1> Preparation of Syrups Syrups containing the honeybush extract or fermented honeybush of the present invention as an active ingredient were prepared according to the composition shown in [Table 5].

TABLE 5

| Constituent | Content (weight part) |
|---|---|
| Honeybush extract or fermented honeybush | 2 |
| Saccharin | 0.8 |
| Sucrose | 25.4 |
| Glycerin | 8 |
| Feed flavor | 0.04 |
| Ethanol | 4 |
| Sorbic acid | 0.4 |
| Distilled water | 60 |

<2-2> Preparation of Tablets

Tablets containing the honeybush extract or fermented honeybush of the present invention as an active ingredient were prepared according to the composition shown in [Table 6].

TABLE 6

| Constituent | Content (weight part) |
|---|---|
| Honeybush extract or fermented honeybush | 250 |
| Lactose | 175.9 |
| Potato starch | 180 |
| Colloidal silicic acid | 32 |
| 10% Gelatin solution | 5 |
| Potato starch | 160 |
| Talc | 50 |
| Magnesium stearate | 5 |

Particularly, 250 weight part of the honeybush extract or fermented honeybush of the present invention, 175.9 weight part of lactose, 180 weight part of potato-starch and 32 weight part of colloidal silicic acid were all mixed together. 10% gelatin solution was added to the mixture, which was then pulverized and filtered with 14-mesh sieve. The pulverized mixture was dried, to which 160 weight part of potato-starch, 50 weight part of talc and 5 weight part of magnesium stearate were added to prepare tablets.

MANUFACTURING EXAMPLE 3

Preparation of Health Foods Containing the Honeybush Extract or Fermented Honeybush as an Active Ingredient Foods containing the honeybush extract or fermented honeybush of the present invention as an active ingredient were prepared as follows.

<3-1> Preparation of Flour Foods 0.5~5.0 weight part of the honeybush extract or fermented honeybush of the present invention was added to the flour.

Health enhancing foods such as bread, cake, cookies, crackers and noodles were prepared with the flour mixture according to the conventional method.

<3-2> Preparation of Soups and Gravies 0.1~5.0 weight part of the honeybush extract or fermented honeybush of the present invention was added to soups and gravies. Health enhancing meat products, soups and gravies were prepared with this mixture by the conventional method.

<3-3> Preparation of Ground Beef

Health enhancing ground beef was prepared by mixing 10 weight part of the honeybush extract or fermented honeybush of the present invention with ground beef according to the conventional method.

<3-4> Preparation of Dairy Products

5~10 weight part of the honeybush extract or fermented honeybush of the present invention was added to milk. Health enhancing dairy products such as butter and ice cream were prepared with the milk mixture according to the conventional method.

<3-5> Preparation of Sun-Sik

Brown rice, barley, glutinous rice and Yulmu (Job's tears) were gelatinized according to the conventional method, dried and pulverized to obtain 60-mesh powders.

Black soybean, black sesame and wild sesame were steamed and dried according to the conventional method and pulverized to obtain 60-mesh powders.

The honeybush extract or fermented honeybush of the present invention was concentrated under reduced pressure, spray-dried and pulverized to obtain 60-mesh dry powders.

Sun-Sik was prepared by mixing the dry powders of the grains, seeds and the honeybush extract or fermented honeybush of the present invention according to the below ratio.

Grains (brown rice: 30 weight part, Yulmu: 15 weight part, barley: 20 weight part), Seeds (wild sesame: 7 weight part, black soybean: 8 weight part, black sesame: 7 weight part), Dry powders of the honeybush extract or fermented honeybush of the present invention (3 weight part),

*Ganoderma lucidum* (0.5 weight part),

*Rehmannia glutinosa* (0.5 weight part)<

3-6> Preparation of Chocolate

Cacao butter 30.0 weight part
Whole milk powder 30.0 weight part
Powdered sugar 41.85 weight part
Lecithin 0.45 weight part
Flavor 0.1 weight part
Honeybush extract or fermented honeybush 0.6 weight part Chocolate containing the honeybush extract or fermented honeybush of the present invention was prepared based on the above compositions and contents by following the conventional method.

<3-7> Preparation of Caramel

Starch syrup 37.43 weight part
White sugar 5.33 weight part
Vegetable oil 9.35 weight part
Emulsifier 0.018 weight part
Salt 0.056 weight part
Skim milk powder 28.07 weight part
Sweetened condensed milk 3.74 weight part
Fresh cream 5.61 weight part
Flavor 0.07 weight part
Honeybush extract or fermented honeybush 10.326 weight part Caramel containing the honeybush extract or fermented honeybush of the present invention was prepared based on the above compositions and contents by following the conventional method.

<3-8> Preparation of Candy

Sugar 50.0 weight part
Starch syrup 33.0 weight part
Citric acid 1.0 weight part
Flavor 0.2 weight part
Honeybush extract or fermented honeybush 0.4 weight part
Water 15.4 weight part Candy containing the honeybush extract or fermented honeybush of the present invention was prepared based on the above compositions and contents by following the conventional method.

<3-9> Preparation of Bread

Egg 2 ea
Sugar 50 weight part
Soft flour 33.5 weight part
Corn starch 6.6 weight part
Baking powder 3.3 weight part
Honeybush extract or fermented honeybush 6.6 weight part bread containing the honeybush extract or fermented honeybush of the present invention was prepared based on the above compositions and contents by following the conventional method.

MANUFACTURING EXAMPLE 4

Preparation of Beverages Containing the Honeybush Extract or Fermented Honeybush as an Active Ingredient <4-1> Preparation of Health Beverages The honeybush extract or fermented honeybush of the present invention (0.5%) was mixed with liquid fructose (0.5%), oligosaccharide (2%), sugar (2%), salt (0.5%), and water (75%). After mixing completely, the mixture was sterilized instantly and filled small containers such as glass bottles, pet bottles, etc, to prepare health beverages.

<4-2> Preparation of Vegetable Juice

Health enhancing vegetable juice was prepared by adding 5 g of the honeybush extract or fermented honeybush of the present invention to 1,000 ml of tomato or carrot juice according to the conventional method.

<4-3> Preparation of Fruit Juice

Health enhancing fruit juice was prepared by adding 1 g of the honeybush extract or fermented honeybush of the present invention to 1,000 ml of apple or grape juice according to the conventional method.

INDUSTRIAL APPLICABILITY

As explained hereinbefore, the honeybush (*Cyclopia intermedia*) extract, the fraction thereof, or fermented honeybush of the present invention has the suppressive effect on skin wrinkle formation caused by UV, so that it can be effectively used for the development and production of cosmetics, skin external preparations, medicines, or health foods for preventing or alleviating skin wrinkles.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for alleviating skin wrinkles in a subject in need thereof comprising administering to the subject a composition comprising an effective amount of a fermented honeybush (*Cydopia intermedia*) extract, wherein the fermented honeybush extract is prepared by the method comprising the following steps:
   i) inoculating animal milk with lactic acid bacteria;
   ii) mixing the inoculated milk of step i) with a carbon source and a honeybush extract or a fraction thereof; and
   iii) fermenting the mixture of step ii) to obtain the fermented honeybush extract.

2. The method of claim 1, wherein the lactic acid bacteria of step i) is *Streptococcus thermophilus*.

3. The method of claim 1, wherein the lactic acid bacteria of step i) is inoculated at a concentration of $3\times10^4$ to $3\times10^6$ CFU/ml.

4. The method of claim 1, wherein the honeybush extract of step ii) is mixed at a ratio of 3 to 10% (v/v) based on the total volume of the inoculum.

5. The method of claim 1, wherein the fermentation of step iii) is performed in an incubator with a temperature of 35 to 38° C. for 1 to 3 days.

6. The method of claim 1, wherein the fermented honeybush extract is administered in combination with an anti-wrinkle agent.

7. The method of claim 6, wherein the anti-wrinkle agent is one or more selected from the group consisting of retinol, retinyl palmitate, adenosine, polyethoxylated retinamide, collagen, and an animal placenta originated protein.

8. The method of claim 1, wherein the composition is a pharmaceutical composition, a cosmetic composition or a functional composition.

* * * * *